(12) United States Patent
Xu

(10) Patent No.: US 7,674,289 B2
(45) Date of Patent: Mar. 9, 2010

(54) BIOLOGICAL ARTIFICIAL LIGAMENT AND METHOD OF MAKING

(75) Inventor: Guo-Feng Xu, Guangzhou (CN)

(73) Assignee: Grandhope Biotech Co., Ltd., Guangzhou (CN)

(*) Notice: Subject to any disclaimer, the term of this patent is extended or adjusted under 35 U.S.C. 154(b) by 557 days.

(21) Appl. No.: 11/494,853

(22) Filed: Jul. 28, 2006

(65) Prior Publication Data
US 2007/0027542 A1 Feb. 1, 2007

(30) Foreign Application Priority Data
Jul. 29, 2005 (CN) ............... 2005 1 0036174

(51) Int. Cl.
A61F 2/08 (2006.01)
A61F 2/02 (2006.01)

(52) U.S. Cl. .............. 623/13.17; 623/13.11; 623/23.72; 623/915

(58) Field of Classification Search ..... 623/13.11–13.2, 623/23.72, 915
See application file for complete search history.

(56) References Cited

U.S. PATENT DOCUMENTS

| | | |
|---|---|---|
| 3,974,526 A | 8/1976 | Dardik et al. |
| 4,083,066 A | 4/1978 | Schmitz et al. |
| 4,319,363 A | 3/1982 | Ketharanathan |
| 4,481,009 A | 11/1984 | Nashef |
| 4,597,766 A | 7/1986 | Hilal et al. |
| 4,765,335 A | 8/1988 | Schmidt et al. |
| 4,793,344 A | 12/1988 | Cumming et al. |
| 5,067,962 A | 11/1991 | Campbell et al. |
| 5,078,744 A | 1/1992 | Chuapil |
| 5,080,670 A | 1/1992 | Imamura et al. |
| 5,217,492 A | 6/1993 | Guire et al. |
| 5,290,217 A | 3/1994 | Campos |
| 5,416,074 A | 5/1995 | Rabaud et al. |
| 5,447,536 A | 9/1995 | Girardot et al. |
| 5,549,666 A | 8/1996 | Hata et al. |
| 5,733,339 A | 3/1998 | Girardot et al. |
| 5,741,283 A | 4/1998 | Fahy |
| 5,758,420 A | 6/1998 | Schmidt et al. |
| 5,902,338 A | 5/1999 | Stone |
| 5,955,110 A | 9/1999 | Patel et al. |
| 5,976,192 A | 11/1999 | McIntyre et al. |
| 5,984,858 A | 11/1999 | Stone |

(Continued)

FOREIGN PATENT DOCUMENTS

CN 1445003 5/1999

(Continued)

OTHER PUBLICATIONS

IPR-PCT/CN2006/003419.

(Continued)

*Primary Examiner*—David Isabella
*Assistant Examiner*—Yashita Sharma
(74) *Attorney, Agent, or Firm*—Raymond Sun

(57) ABSTRACT

A prosthesis for implantation into a human body is made by a method that includes the steps of providing a natural animal ligament or tendon that has a substrate, crosslinking and fixing the substrate, minimizing the antigens from the substrate, tanning the substrate to improve its mechanical properties, and coupling an active layer to the substrate.

8 Claims, 1 Drawing Sheet

U.S. PATENT DOCUMENTS

| | | |
|---|---|---|
| 6,008,292 A | 12/1999 | Lee et al. |
| 6,090,995 A | 7/2000 | Reich et al. |
| 6,106,555 A | 8/2000 | Yang |
| 6,117,979 A | 9/2000 | Hendriks et al. |
| 6,177,514 B1 | 1/2001 | Pathak et al. |
| 6,241,981 B1 | 6/2001 | Cobb et al. |
| 6,251,117 B1 | 6/2001 | Kringel et al. |
| 6,458,889 B1 | 10/2002 | Trolisas et al. |
| 6,572,650 B1 | 6/2003 | Abraham et al. |
| 7,053,051 B2 | 5/2006 | Hendriks et al. |
| 7,060,103 B2 | 6/2006 | Carr, Jr. et al. |
| 7,077,851 B2 | 7/2006 | Lutze et al. |
| 2002/0042473 A1 | 4/2002 | Trolisas et al. |
| 2002/0081564 A1 | 6/2002 | Levy et al. |
| 2002/0091445 A1* | 7/2002 | Sung et al. ............... 623/13.17 |
| 2002/0099448 A1 | 7/2002 | Hiles et al. |
| 2002/0103542 A1 | 8/2002 | Bilbo |
| 2002/0138152 A1 | 9/2002 | Francis et al. |
| 2003/0013989 A1 | 1/2003 | Obemiller et al. |
| 2004/0202625 A1 | 10/2004 | Daniloff et al. |
| 2005/0119736 A1 | 6/2005 | Zilla |
| 2005/0136543 A1 | 6/2005 | Torres et al. |
| 2008/0195229 A1 | 8/2008 | Quijano et al. |

FOREIGN PATENT DOCUMENTS

| | | |
|---|---|---|
| CN | 1237889 | 12/1999 |
| CN | 1267201 | 9/2000 |
| CN | 1313741 | 9/2001 |
| CN | 1330528 | 1/2002 |
| CN | 1456363 | 11/2003 |
| CN | 1473551 | 2/2004 |
| CN | 1556715 | 12/2004 |
| CN | 1579342 | 2/2005 |
| WO | WO9417851 | 8/1994 |
| WO | WO 9822158 | 5/1998 |
| WO | WO 0032250 | 6/2000 |
| WO | WO0232327 | 4/2002 |

OTHER PUBLICATIONS

IPR-PCT/CN2006/003442.
IPR-PCT/CN2006/003443.
IPR-PCT/CN2006/003444.
IPR-PCT/CN2006/001878.
IPR-PCT/CN2006/001879.
IPR-PCT/CN2006/001880.

* cited by examiner

BIOLOGICAL ARTIFICIAL LIGAMENT AND METHOD OF MAKING

BACKGROUND OF THE INVENTION

1. Field of the Invention

The present invention relates to a medical prosthesis for human implantation, and in particular, to an artificial ligament which is utilized to rebuild the ligament of a patient with a torn ligament.

2. Description of the Prior Art

A torn ligament is one of the most common sport injuries, and the anterior cruciate ligaments located at the knee joints have a very high incidence of tears during sport activities. The consequences of these tears are usually very severe which can lead to further structural damage such as ligament erosion, impaired joint function, and even disability, if treatment is not performed promptly and properly. Previously, surgeons attempted treatment by sewing the torn parts, but because ligaments have poor adherence and healing power, almost all of these attempts failed, so that such practices were abandoned.

Therefore, surgeons placed their hopes on rebuilding ligaments by transplantation. However, the biggest drawback of such a method is that it increases autoinjuries and leaves complications, sometimes to the extent that the drawbacks outweigh the benefits.

For example, using the patellar tendon as a replacement (in general, the connecting bones are also removed in the form of bone-patellar tendon-bone) for transplantation easily causes complications such as knee pain, patellar tendon contraction, and tendonitis, and complete success cannot be insured if the procedure is not done perfectly.

Another method uses tendons or ligaments as replacements by allogenic transplantation (i.e, from a fresh cadaver), but this method has two important drawbacks: (1) the source is scarce, and (2) the support measures are out-of-date, and very often the specimens are simply stored in low temperature refrigerators and utilized in transplantations after simple sterilization by immersing in a sterilizing solution, which cannot effectively eliminate antigens and kill all the bacteria and viruses which might be present in the cadaver body, nor can it prevent rejection or eliminate the risk of infections after transplantation.

Yet another method uses artificial ligaments as replacements for transplantation, and synthetic polymeric substances such as long strings or knitted bands of polyester, nylons, polytetrafluoroethylene, etc., are generally utilized as the replacements for transplantation, which normally produce good short-term effects. However, these synthetic polymers are different from body tissues with respect to their composition and structure, so that the risk of having aseptic inflammation due to chronic rejection is ever present. More importantly, polymeric materials have inherent creep deformation in nature and after a certain time of playing the function of ligaments, they are irreversibly elongated and lose the elastic function of ligaments. In recent years, attempts were made to prepare artificial tendons and ligaments from bovine tendons, and the specimens were utilized after simple freezing at low temperature (−80° C.), defatting and fixation by glutaraldehyde. Glutaraldehyde fixes proteins by crosslinking them and forming aldehyde acetals, but aldehyde acetal is not very stable and the resistance of the fixed substance to degradation is poor, which results in loss of the inherent mechanical strength due to degradation. In addition, the degradation slowly releases glutaraldehyde and generates toxic aldehyde radicals, and this is compounded by the problem that there is no antigenic treatment in the process to effectively eliminate the antigenicity, so that failures are often experienced due to chronic rejection when the specimens are transplanted into the body.

In light of the above reasons, there still remains a need for an artificial ligament which is utilized to rebuild the ligament of a patient with a torn ligament.

SUMMARY OF THE DISCLOSURE

It is an object of the present invention to provide safe and reliable biological artificial ligaments having high biocompatibility, stability, and resistance to degradation, and which capable of accelerating the body's regenerative repair.

It is another object of the present invention to provide a method of preparing such an artificial ligament.

In order to accomplish the objects of the present invention, the present invention provides a biological prosthesis for implantation into a human body which is made by a method that includes the steps of providing a natural animal ligament or tendon that has a substrate, crosslinking and fixing the substrate, minimizing the antigens from the substrate, and coupling an active layer to the substrate.

DETAILED DESCRIPTION OF THE PREFERRED EMBODIMENTS

Figure 1:
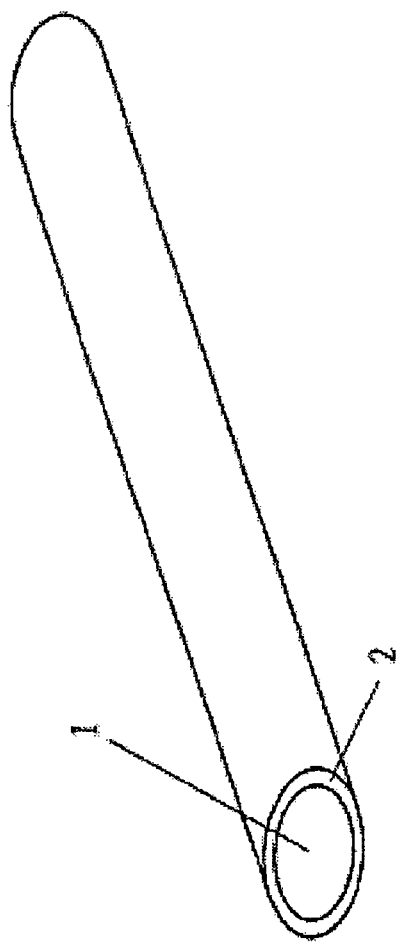
FIG. 1 is a perspective view of an artificial ligament according to one embodiment of the present invention.

The following detailed description is of the best presently contemplated modes of carrying out the invention. This description is not to be taken in a limiting sense, but is made merely for the purpose of illustrating general principles of embodiments of the invention. The scope of the invention is best defined by the appended claims.

The present invention provides a biological artificial ligament having a substrate made of an animal soft tissue, such as a ligament or a tendon, that is crosslinked and fixed with a fixative, treated to minimize antigens, subjected to a tanning process, and then coated with a surface layer containing an active layer. Although the present invention is being described in connection with animal ligaments, the principles of the present invention also apply to the various applications described at the end of this disclosure.

Animal ligament or tendon tissues are easily degraded or decomposed by microorganisms, so that crosslinking and fixation with a fixative is required. Conventionally, glutaraldehyde is utilized as a fixative, but glutaraldehyde produces toxic radicals. However, aldehydes undergo crosslinking with proteins through the acetal reaction and toxic aldehydes are released when the crosslinked products are degraded, so that products fixed with an aldehyde have long-term residual toxicity. When epoxides, diamides, diisocyanates or carbodiimides are utilized as fixatives in place of aldehydes, this toxicity problem can be eliminated. When an epoxide is utilized, for example, proteins are crosslinked through a ring opening reaction of the epoxide, and reverse ring closure to form the epoxide back does not readily occur, and the degradation products are diols and polyols which can be metabolized by the body so that there is no risk of toxic aldehyde radicals. The stability of the animal ligaments after treatment is also higher than those fixed with aldehydes. According to modern immunological theory, the antigenicity of animal tissues stems mainly from active groups located at specific sites and in specific conformations, and these active groups include —OH, —NH2, —SH, etc. The specific conformations result mainly from some specific hydrogen bonding formed by spiral protein chains. The specific sites and conformations are called antigen determinants. When treating the animal ligaments, one or several small, active reagents (e.g., acid anhydrides, acid chlorides, acylamides, epoxides, etc.) which can readily react with these groups are used to bind and block these groups, which in turn effectively minimizes the antigenicity, and in the meantime strong hydrogen bonding reagents (e.g., guanidine compounds) are utilized to form new hydrogen bonds and replace the inherent hydrogen bonding of the specific conformations, which changes the specific conformations and further effectively minimizes the antigenicity. The structure of the animal ligaments cannot be easily altered after they have been crosslinked and fixed by non-aldehyde fixatives such as epoxides, and the tissues are not easily degraded or decomposed, and collagenase only begins to phagocytize and degrade them due to the synergistic effect of fibrinolysin and kallikrein released by nascent tissues, which means that the new ligament tissues have sufficient time to grow and take hold, while no toxic radicals remain. The immunogenicity is effectively minimized by blocking the active groups in the proteins and changing the conformation, and the resulting substrate has no chronic immune rejection while having excellent biocompatibility. Furthermore, the tissue compatibility is improved by modifying the surface by incorporating an active component (as described below), including a specific polypeptide and glucosaminoglycan. The specific polypeptide and glucosaminoglycan have broad spectrum adhesion and affinity for growth factors, or are capable of activating undifferentiated cells to undergo oriented differentiation, which promotes regeneration and repairs the organic ligaments.

Method

A method of preparing the biological artificial ligaments according to the present invention comprises the following steps, using natural animal ligaments as the substrate:

1. Screening of materials: Fresh animal ligaments and tendons are collected.

2. Pretreatment: Initial sterilization is performed using a broad spectrum, highly-effective, low-toxicity bacteriacide, followed by trimming irregular portions.

3. Defatting: The fatty substances in the substrate are extracted with organic solvents using known tissue-treatment techniques.

4. Fixation: The protein molecules in the substrate are crosslinked and fixed using a fixative, as described in greater detail hereinbelow.

5. Minimizing antigens: An active reagent is utilized to block the specific active groups such as —OH, —NH2, —SH, etc., in the proteins of the substrate, and a reagent with strong hydrogen bonding power is utilized to replace the specific hydrogen bonding in the spiral chains of the protein molecules in the substrate and alter its specific conformation.

6. Coupling of active layer: An active surface layer containing a specific polypeptide or glucosaminoglycan capable of adhering to growth factors is incorporated on the surface layer using a coupling agent. This step is utilized for the optimal design.

Broad Spectrum Antibacterial Agents

The broad spectrum antibacterial agents in step 2 of the above method can be selected among benzalkonium bromide, sodium azide and chlorhexidine.

Organic Solvents

The organic solvents in step 3 of the above method can be selected among chloroform, ethyl acetate, anhydrous alcohol and mixtures thereof.

Fixative

The fixative applied in step 4 of the above method may be an epoxy compound that has a hydrocarbon backbone, that is water-soluble, and which does not contain an ether or ester linkage in its backbone. This fixative is described in U.S. Pat. No. 6,106,555, whose entire disclosure is incorporated by this reference as though set forth fully herein. Examples include an epoxide, a diamide, a diisocyanate, or a carbodiimide, in that the epoxide may be a monocyclic epoxide, or a bicyclic epoxide, or it may be a low poly(epoxide) (such as low poly (ethylene oxide), poly(propylene oxide) or a glycidyl ether).

Active Reagents

The active reagents in step 5 of the above method may be low molecular weight organic acid anhydrides, acyl chlorides, acylamides or monocyclic oxides, and the reagents having strong hydrogen bonding power are guanidine compounds.

Active Layer

The active layer in step 6 of the above method can contain a specific polypeptide capable of adhering to and accumulating growth factors, so that angiogenesis can be promoted. Examples of growth factors for blood vessels that can adhere to and accumulate include vascular endothelial growth factor (VEGF), fibroblast growth factor (FGF), platelet-derived growth factor (PDGF-bb) and vascular permeability factor (VPF). One example of the polypeptide is the polypeptide consisting of 16 lysines (K16), glycine (G), arginine (R), aspartic acid (D), serine (S), proline (P) and cysteine (C), and sequence of the composition is K16-G-R-G-D-S-P-C. The glucosaminoglycan can be hyaluronic acid, chondroitin sulfate, dermatan sulfate, heparin, acetylated heparin sulfate or keratin sulfate Coupling Agent for Active Layer The coupling agent utilized for coupling the polypeptide or the glucosaminoglycan in step 6 of the above method may be a diamide, acid anhydride, epoxide, or other bifunctional reagent capable of undergoing a condensation reaction with —NH2, —OH, —COOH, etc.

The present invention provides the following advantages:

1. The biocompatibility is excellent without immune rejection, and the composition resembles that of human ligaments while the degradation products can be absorbed and utilized by new ligament tissues.

2. The stability is high and it is not easily degraded under normal conditions, and collagenase only begins to phagocytize and degrade it under the synergistic effect of fibrinolysin and kallikrein released by nascent tissues, resulting in synchronized tissue degradation and regeneration.

3. The mechanical strength is strong enough to completely satisfy the mechanical requirements for a ligament.

4. An active component such as specific polypeptide or glucosaminoglycan is incorporated to modify the surface activity through coupling, so that growth factors can actively adhere to, and accumulate and activate undifferentiated cells to undergo oriented differentiation and improve the regenerative ability of the ligament, making it an excellent support and carrier for ligament repair. This characteristic is significantly better than the artificial ligaments of synthetic materials.

EXAMPLE 1

Figure 2:
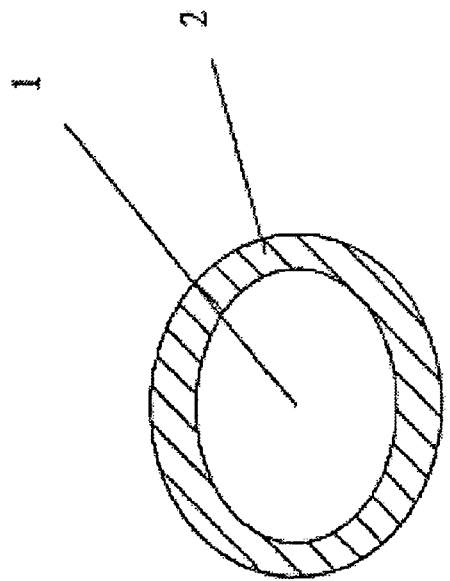
FIG. 2 is a cross-sectional view of the artificial ligament of FIG. 1.

Referring to FIGS. 1 and 2, a biological artificial ligament comprising a substrate 1 is formed with an animal ligament or tendon crosslinked and fixed with an epoxide and treated to minimize antigens. An activated surface layer 2 is formed on the surface of the substrate 1 by coupling a specific polypeptide capable of adhering to and accumulating growth factors. In this example, the polypeptide is the polypeptide consisting of 16 lysines (K16), glycine (G), arginine (R), aspartic acid (D), serine (S), proline (P) and cysteine (C), and said glucosaminoglycan is hyaluronic acid, chondroitin sulfate, dermatan sulfate, heparin, acetylated heparin sulfate or keratin sulfate. This biological artificial ligament can be made from the following steps:

1. Screening of materials: Fresh animal ligaments and tendon are collected by professional technicians from regulated and well-managed slaughterhouses while special efforts are made to avoid direct contact with pollutants.

2. Pretreatment: Initial sterilization is performed using broad spectrum, highly-effective and low-toxicity bacteriacides such as benzalkonium bromide, sodium azide and chlorhexidine, followed by eliminating impurities and trimming irregular portions.

3. Defatting: The fatty substances in the substrate 1 are extracted with organic solvents such as chloroform, acetone, ethyl acetate, diethyl ether, anhydrous alcohol or mixtures thereof.

4. Fixation: The protein molecules in the substrate 1 are crosslinked and fixed using a bicyclic epoxide as a fixative

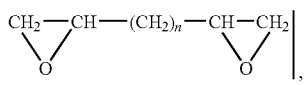

where n=0-10.

5. Minimizing antigens: The specific and active groups, —OH or —$NH_2$ or —SH, of the proteins in the substrate 1 are blocked using low molecular weight, active reagents such as organic acid anhydrides, acyl chlorides, acylamides or monocyclic epoxides, and the specific hydrogen bonding on the spiral chains of the protein molecules of the substrate 1 is replaced using a strong hydrogen bonding reagent such as a guanidine compound, which alters the specific conformation.

6. Surface modification: An active ingredient such as a specific polypeptide is deposited on the surface of the substrate 1 through coupling using a diamide, acid anhydride, epoxide or other bifunctional reagent capable of undergoing condensation with —$NH_2$, —OH, —COOH, etc., to form active surface layer 2 on the surface of the substrate 1.

Other Applications

The method of the present invention can also be utilized to treat a variety of other prosthetic devices.

For example, the method of the present invention can be utilized for the following applications:

1. prosthetic tendons using animal tendons as the raw material;

2. surgical repair patch and dural graft, using animal pericardium or other similar membranes as the raw material;

3. urinary bladder repair patch using animal small intestine submucosa or other similar membranes as the raw material; and 4. skin grafts, using animal skin or other similar membranes as the raw material.

All the elements, chemicals and steps described herein can be utilized for these four applications.

While the description above refers to particular embodiments of the present invention, it will be understood that many modifications may be made without departing from the spirit thereof. The accompanying claims are intended to cover such modifications as would fall within the true scope and spirit of the present invention.

What is claimed is:

1. A natural animal ligament or tendon isolated from its host that has a substrate that has: (i) been fixed with crosslinking reagents, (ii) residual specific active groups in protein molecules of the substrate that have been blocked by at least one active reagent after fixation by the crosslinking reagents, (iii) specific conformation of protein molecules of the substrate altered by a reagent with strong hydrogen bonding power, and (iv) an active layer coupled thereto, the active layer including either a polypeptide or a glucosaminoglycan that has the ability to adhere growth factors after implantation.

2. The ligament or tendon of claim 1, wherein the substrate is fixed by an epoxy compound that has a hydrocarbon backbone, that is water-soluble, and which does not contain an ether or ester linkage in its backbone.

3. The ligament or tendon of claim 1, wherein the at least one active reagent to block specific active groups in the protein molecules of the substrate can be acid anhydrides, acid chlorides, or acylamides.

4. The ligament or tendon of claim 1, wherein the reagent with strong hydrogen bonding power is a guanidine compound.

5. A ligament or tendon for implantation into a human body, the ligament made by a method comprising:

isolating from a host a natural animal ligament or tendon that has a substrate;

crosslinking and fixing the substrate;

blocking residual specific active groups in protein molecules of the substrate after fixation by applying at least one active reagent;

altering the specific conformation of protein molecules of the substrate by a reagent with strong hydrogen bonding power; and coupling an active layer to the substrate that includes either a polypeptide or a glucosaminoglycan that has the ability to adhere growth factors after implantation.

6. The ligament or tendon of claim 5, wherein the substrate is fixed by an epoxy compound that has a hydrocarbon backbone, that is water-soluble, and which does not contain an ether or ester linkage in its backbone.

7. The ligament or tendon of claim 5, wherein the at least one active reagent to block specific active groups in the protein molecules of the substrate can be acid anhydrides, acid chlorides, or acylamides.

8. The ligament or tendon of claim 5, wherein the reagent with strong hydrogen bonding power is a guanidine compound.

* * * * *